(12) United States Patent
Lulevich et al.

(10) Patent No.: US 10,384,169 B2
(45) Date of Patent: Aug. 20, 2019

(54) SUPPORTED CARBON NANOTUBE MEMBRANES AND THEIR PREPARATION METHODS

(71) Applicant: Porifera, Inc., Hayward, CA (US)

(72) Inventors: Valentin Lulevich, Oakland, CA (US); Olgica Bakajin, Berkeley, CA (US)

(73) Assignee: Porifera, Inc., Hayward, CA (US)

( * ) Notice: Subject to any disclaimer, the term of this patent is extended or adjusted under 35 U.S.C. 154(b) by 75 days.

(21) Appl. No.: 15/522,701

(22) PCT Filed: Oct. 30, 2015

(86) PCT No.: PCT/US2015/058417
§ 371 (c)(1),
(2) Date: Apr. 27, 2017

(87) PCT Pub. No.: WO2016/070103
PCT Pub. Date: May 6, 2016

(65) Prior Publication Data
US 2017/0333847 A1    Nov. 23, 2017

Related U.S. Application Data

(60) Provisional application No. 62/073,788, filed on Oct. 31, 2014.

(51) Int. Cl.
*A61K 9/00* (2006.01)
*B82Y 5/00* (2011.01)
(Continued)

(52) U.S. Cl.
CPC .......... *B01D 69/147* (2013.01); *A61K 9/0092* (2013.01); *A61K 31/465* (2013.01);
(Continued)

(58) Field of Classification Search
None
See application file for complete search history.

(56) References Cited

U.S. PATENT DOCUMENTS 3,721,621 A    3/1973    Hough
4,326,509 A    4/1982    Usukura
(Continued)

FOREIGN PATENT DOCUMENTS

CN    101228214 A    7/2008
JP    S55149682 A    11/1980
(Continued)

OTHER PUBLICATIONS

U.S. Appl. No. 15/739,657, Methods of Dewatering of Alcoholic Solutions via Forward Osmosis and Related Systems, filed Dec. 22, 2017.
(Continued)

*Primary Examiner* — Krishnan S Menon
(74) *Attorney, Agent, or Firm* — Dorsey & Whitney LLP

(57) ABSTRACT

Membranes are described that may include aligned carbon nanotubes coated with an inorganic support layer and a polymeric matrix. Methods of membrane fabrication are described that may include coating an aligned carbon nanotube array with an inorganic support layer followed by infiltration with a polymeric solvent or solution. The support carbon nanotube membrane may have improved performance for separations such as desalination, drug delivery, or pharmaceuticals.

17 Claims, 4 Drawing Sheets

(51) Int. Cl.

| | | |
|---|---|---|
| C07K 1/34 | (2006.01) | |
| A61K 38/28 | (2006.01) | |
| A61K 45/00 | (2006.01) | |
| B01D 67/00 | (2006.01) | |
| B01D 69/12 | (2006.01) | |
| B01D 69/14 | (2006.01) | |
| B01D 71/02 | (2006.01) | |
| B01D 71/46 | (2006.01) | |
| B82Y 30/00 | (2011.01) | |
| B82Y 40/00 | (2011.01) | |
| C07H 21/04 | (2006.01) | |
| A61K 31/465 | (2006.01) | |
| C01B 32/168 | (2017.01) | |

(52) U.S. Cl.
CPC ............ *A61K 38/28* (2013.01); *A61K 45/00* (2013.01); *B01D 67/0072* (2013.01); *B01D 67/0079* (2013.01); *B01D 69/12* (2013.01); *B01D 69/148* (2013.01); *B01D 71/021* (2013.01); *B01D 71/46* (2013.01); *C01B 32/168* (2017.08); *C07H 21/04* (2013.01); *C07K 1/34* (2013.01); *B82Y 5/00* (2013.01); *B82Y 30/00* (2013.01); *B82Y 40/00* (2013.01); *C01B 2202/08* (2013.01); *Y10S 977/742* (2013.01); *Y10S 977/753* (2013.01); *Y10S 977/847* (2013.01)

(56) References Cited

U.S. PATENT DOCUMENTS

| | | | |
|---|---|---|---|
| 4,428,720 A | 1/1984 | Van Erden et al. | |
| 4,454,176 A | 6/1984 | Buckfelder et al. | |
| 4,618,533 A | 10/1986 | Steuck | |
| 4,792,402 A | 12/1988 | Fricker | |
| 5,593,738 A | 1/1997 | Ihm et al. | |
| 6,261,879 B1 | 7/2001 | Houston et al. | |
| 6,406,626 B1 | 6/2002 | Murakami et al. | |
| 6,413,070 B1 | 7/2002 | Meyering et al. | |
| 6,513,666 B2 | 2/2003 | Meyering et al. | |
| 6,755,970 B1 | 6/2004 | Knappe et al. | |
| 6,849,184 B1 | 2/2005 | Lampi et al. | |
| 6,884,375 B2 | 4/2005 | Wang et al. | |
| 6,992,051 B2 | 1/2006 | Anderson | |
| 7,205,069 B2 | 4/2007 | Smalley et al. | |
| 7,445,712 B2 | 11/2008 | Herron | |
| 7,611,628 B1 | 11/2009 | Hinds, III | |
| 7,627,938 B2 | 12/2009 | Kim et al. | |
| 7,901,578 B2 | 3/2011 | Pruet | |
| 7,955,506 B2 | 6/2011 | Bryan et al. | |
| 8,029,857 B2 | 10/2011 | Hoek et al. | |
| 8,038,887 B2 | 10/2011 | Bakajin et al. | |
| 8,177,978 B2 | 5/2012 | Kurth et al. | |
| 8,252,350 B1 | 8/2012 | Cadwalader et al. | |
| 8,356,717 B2 | 1/2013 | Waller, Jr. et al. | |
| 8,518,276 B2 | 8/2013 | Striemer et al. | |
| 8,567,612 B2 | 10/2013 | Kurth et al. | |
| 8,920,654 B2 | 12/2014 | Revanur et al. | |
| 9,216,391 B2 | 12/2015 | Revanur et al. | |
| 9,227,360 B2 | 1/2016 | Lulevich et al. | |
| 2002/0063093 A1 | 5/2002 | Rice et al. | |
| 2003/0038074 A1 | 2/2003 | Patil | |
| 2004/0004037 A1 | 1/2004 | Herron | |
| 2004/0071951 A1 | 4/2004 | Jin | |
| 2005/0142385 A1 | 6/2005 | Jin | |
| 2006/0144789 A1 | 7/2006 | Cath et al. | |
| 2006/0233694 A1 | 10/2006 | Sandhu et al. | |
| 2008/0149561 A1 | 6/2008 | Chu et al. | |
| 2008/0210370 A1 | 9/2008 | Smalley et al. | |
| 2008/0223795 A1 | 9/2008 | Bakajin et al. | |
| 2008/0236804 A1 | 10/2008 | Cola et al. | |
| 2008/0290020 A1 | 11/2008 | Marand et al. | |
| 2009/0078640 A1 | 3/2009 | Chu et al. | |
| 2009/0214847 A1 | 8/2009 | Maruyama et al. | |
| 2009/0250392 A1 | 10/2009 | Thorsen et al. | |
| 2009/0272692 A1 | 11/2009 | Kurth et al. | |
| 2009/0283475 A1 | 11/2009 | Hylton et al. | |
| 2009/0308727 A1 | 12/2009 | Kirts | |
| 2009/0321355 A1 | 12/2009 | Ratto et al. | |
| 2010/0025330 A1 | 2/2010 | Ratto et al. | |
| 2010/0051538 A1 | 3/2010 | Freeman et al. | |
| 2010/0059433 A1 | 3/2010 | Freeman et al. | |
| 2010/0062156 A1 | 3/2010 | Kurth et al. | |
| 2010/0140162 A1 | 6/2010 | Jangbarwala | |
| 2010/0155333 A1 | 6/2010 | Husain et al. | |
| 2010/0206811 A1 | 8/2010 | Ng et al. | |
| 2010/0212319 A1 | 8/2010 | Donovan | |
| 2010/0224550 A1 | 9/2010 | Herron | |
| 2010/0224561 A1 | 9/2010 | Marcin | |
| 2010/0320140 A1 | 12/2010 | Nowak et al. | |
| 2011/0036774 A1 | 2/2011 | McGinnis | |
| 2011/0057322 A1 | 3/2011 | Matsunaga et al. | |
| 2011/0073540 A1 | 3/2011 | McGinnis et al. | |
| 2011/0132834 A1 | 6/2011 | Tomioka et al. | |
| 2011/0186506 A1 | 8/2011 | Ratto et al. | |
| 2011/0220574 A1 | 9/2011 | Bakajin et al. | |
| 2011/0284456 A1 | 11/2011 | Brozell et al. | |
| 2011/0311427 A1 | 12/2011 | Hauge et al. | |
| 2012/0043274 A1 | 2/2012 | Chi et al. | |
| 2012/0080378 A1 | 4/2012 | Revanur et al. | |
| 2012/0080381 A1 | 4/2012 | Wang et al. | |
| 2012/0118827 A1 | 5/2012 | Chang et al. | |
| 2012/0241371 A1 | 9/2012 | Revanur et al. | |
| 2012/0251521 A1 | 10/2012 | Rostro et al. | |
| 2012/0267297 A1 | 10/2012 | Iyer | |
| 2012/0273421 A1 | 11/2012 | Perry et al. | |
| 2013/0095241 A1 | 4/2013 | Lulevich et al. | |
| 2013/0203873 A1 | 8/2013 | Linder et al. | |
| 2013/0220581 A1 | 8/2013 | Herron et al. | |
| 2014/0015159 A1 | 1/2014 | Lazar et al. | |
| 2014/0302579 A1 | 10/2014 | Boulanger et al. | |
| 2014/0319056 A1 | 10/2014 | Fuchigami et al. | |
| 2015/0064306 A1 | 3/2015 | Tatera et al. | |
| 2015/0273399 A1 | 10/2015 | Roh et al. | |
| 2016/0038880 A1 | 2/2016 | Benton et al. | |
| 2016/0136577 A1 | 5/2016 | McGovern et al. | |
| 2016/0136578 A1 | 5/2016 | McGovern et al. | |
| 2016/0136579 A1 | 5/2016 | McGovern et al. | |
| 2016/0230133 A1 | 8/2016 | Peterson et al. | |

FOREIGN PATENT DOCUMENTS

| | | |
|---|---|---|
| JP | S5959213 A | 4/1984 |
| JP | 62-140620 A | 6/1987 |
| JP | 2005-138028 A | 6/2005 |
| JP | 2010094641 A | 4/2010 |
| WO | 9962623 | 12/1999 |
| WO | 0213955 A1 | 2/2002 |
| WO | 2008/137082 A1 | 11/2008 |
| WO | 2009/035415 | 3/2009 |
| WO | 2009039467 A1 | 3/2009 |
| WO | 2009129354 A2 | 10/2009 |
| WO | 2010006196 A2 | 1/2010 |
| WO | 2010144057 A1 | 12/2010 |
| WO | 2011028541 A1 | 3/2011 |
| WO | 2012/047282 | 4/2012 |
| WO | 2012/135065 | 10/2012 |
| WO | 2013/059314 | 4/2013 |
| WO | 2014063149 A1 | 4/2014 |
| WO | 2014/071238 A1 | 5/2014 |
| WO | 2016070103 A1 | 5/2016 |
| WO | 2016210337 A2 | 12/2016 |

OTHER PUBLICATIONS

International Search and Written Opinion received for PCT US2015/58417 dated Feb. 3, 2016.

Akthakul, et al., "Antifouling polymer membranes with subnanometer size selectivity", Macromolecules 37, Sep. 3, 2004, 7663-7668.

(56) References Cited

OTHER PUBLICATIONS

Cath, et al., "Forward osmosis: principles, applications and recent developments", Journal of Membrane Science 281, May 31, 2006, 70-87.

Li, et al., "Electronic properties of multiwalled carbon nanotubes in an embedded vertical array", Applied Physics Letters vol. 81, No. 5, Jul. 2002, 910-912.

Mandal, et al., "Drug delivery system based on chronobiology—a review", Journal of Controlled Release 147, Aug. 4, 2010, 314-325.

McCutcheon, et al., "Influence of membrane support layer hydrophobicity on water flux in osmotically driven membrane processes", Journal of Membrane Science, Mar. 2008, 458-466.

McEuen, P. et al., "Single-Walled Nanotubes Electronics", IEEE Transactions on Nanotechnology, Vo. 1, No. 1, Mar. 2002.

Santus, et al., "Osmotic drug delivery: a review of the patent literature", Journal of Controlled Release 35, Jul. 1995, 1-21.

Sotthivirat, et al., "Controlled porosity-osmotic pump pellets of a poorly water-soluble drug using sulfobutylether-b-cyclodestrin, (SBE)_7M-b-CD, as a solubilizing and osmotic agent", Journal of Pharmaceutical Sciences vol. 96, No. 9, Sep. 2007, 2364-2374.

Yip, Nagai Y. et al., "High Performance Thin-Film Composite Forward Osmosis Membrane", Environmental Science & Technology, vol. 44, No. 10, 2010, Apr. 21, 2010, 3812-3818.

Zhao, et al., "Modification of porous poly (vinylidene fluoride) membrane using amphiphilic polymers with different structures in phase inversion process", Journal of Membrane Science 310, Mar. 2008, 567-576.

SUPPORTED CARBON NANOTUBE MEMBRANES AND THEIR PREPARATION METHODS

CROSS-REFERENCE TO RELATED APPLICATIONS

This application is a 35 U.S.C. § 371 National Stage Application of PCT Application No. PCT/US2015/058417, filed on Oct. 30, 2015, which claims filing benefit under 35 U.S.C. § 119(e) of the earlier filing date of U.S. Provisional Application 62/073,788, filed Oct. 31, 2014. All aforementioned applications are hereby incorporated by reference in their entirety for any purpose.

BACKGROUND

Carbon nanotube membranes are known for their superior membrane performance. However, the fabrication of carbon nanotube membranes still has significant challenges. Defects in carbon nanotubes may result in membranes with poor performance or uneven characteristics. Infiltration of an aligned carbon nanotube array with a polymeric solution may induce defects in the nanotubes and reduce the membrane performance.

SUMMARY

Example carbon nanotube membranes are described herein. An example carbon nanotube membrane includes an aligned array of carbon nanotubes, an inorganic support material coating at least a portion of a length of the carbon nanotubes in the aligned array, and a polymer material disposed between the carbon nanotubes. In some examples, the inorganic support material comprises inorganic oxide. In some examples, the inorganic support material comprises alumina. In some examples, the polymer material comprises epoxy. In some examples, the polymer material is disposed in spaces between the inorganic support material coating at least a portion of a length of the carbon nanotubes. The example carbon nanotube membrane may further include a mesh or fabric support supporting the polymer material.

In some examples, the aligned array of carbon nanotubes, the inorganic support material, and the polymer form a carbon nanotube polymer composite having a surface, and the surface is planarized. In some examples, the aligned array of carbon nanotubes have open ends at the surface. In some examples, the aligned array of carbon nanotubes extend through a thickness of the carbon nanotube polymer composite.

Examples of methods are described herein. An example method includes providing an aligned array of nanotubes, depositing an inorganic support material on at least some walls of the nanotubes in the aligned array, infiltrating a polymer precursor around the aligned array of nanotubes including the inorganic support material on at least some walls, and curing the polymer precursor to form a polymer nanotube composite. In some examples, the aligned array of nanotubes is provided by growing the aligned array of nanotubes on a substrate. In some examples, atomic layer deposition is used to deposit the inorganic support material. In some examples, chemical vapor deposition is used to deposit the inorganic support material.

The example method may further include planarizing the polymer nanotube composite by mechanical polishing.

In some examples, the aligned array of nanotubes are provided on a substrate, and the example method may further include releasing the polymer nanotube composite from the substrate.

In some examples, the inorganic support material includes alumina, titania, silica, hafnia, or combinations thereof. In some examples, the polymer precursor includes an epoxy resin.

DETAILED DESCRIPTION

Figure 1:
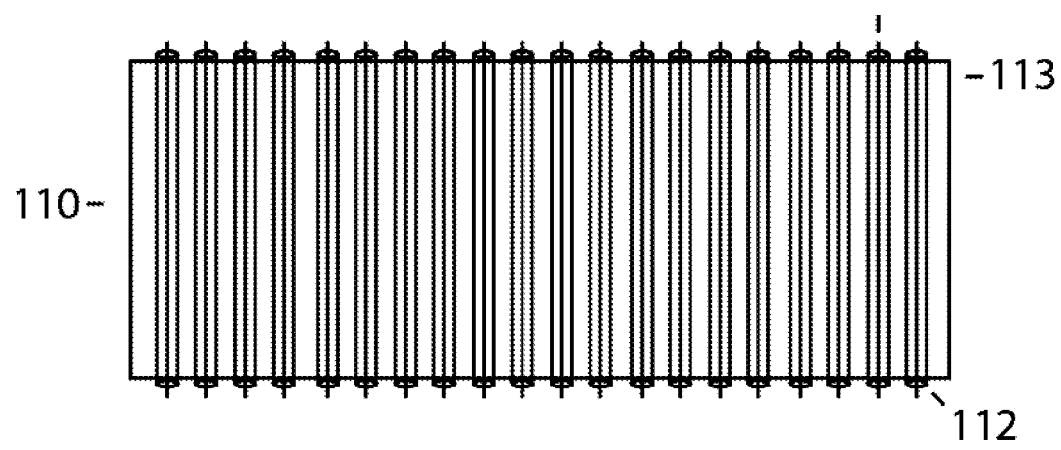
FIG. 1 is a schematic of a nanotube membrane that may include aligned carbon nanotubes coated with an inorganic support layer and a polymer fill.

Certain details are set forth herein to provide a sufficient understanding of embodiments of the invention. However, it will be clear to one skilled in the art that embodiments of the invention may be practiced without various of these particular details. In some instances, well-known membrane components have not been shown in detail in order to avoid unnecessarily obscuring the described embodiments of the invention.

The performance of carbon nanotube membranes is typically determined by transport though the nanotube pore as well as the density of open defect-free nanotube channels. In some cases, the nanotube channels may be blocked or plugged, resulting in a small percentage, 1% for example, of the channels being involved in ion transport. A typical nanotube forest grown with iron catalyst and alumina support layer produces tube densities up to $10^{12}$ tubes/cm$^2$. However, ion transport measurements suggest that the density of tubes involved in ion transport in membranes may achieve only $10^9$ tubes/cm$^2$ in some instances. Even in high quality, low defect single-walled carbon nanotube (SWCNT) based membranes the number of working tubes may be low in some examples. This may be due to the introduction of defects not only during nanotube growth but also during membrane infiltration with polymer solution. The solution may cause flexible hydrophobic tubes to bend and pinch the nanotube channel. Therefore, it may be advantageous for nanotubes (and especially flexible SWCNTs) to be reinforced with a support before infiltrating them. While one possible mechanism (e.g. bending of tubes) has been discussed to explain why a low number of nanotubes may be involved in ion transport in some examples, the discussion of mechanisms is provided by way of example and is not intended to limit the scope of this disclosure or claims. Similarly advantages of methods and membranes described herein (e.g. improved percentage of tubes involved in transport) are provided by way of example, and it is to be understood that not all methods or membranes described herein may exhibit all, or even any, of the described advantages Nanotube reinforcement may increase the number of 'working' channels in the membrane. Initial studies of ion transport through an example nanotube membrane where only the top 5-15 μm were coated by atomic layer deposition (ALD) revealed that the membrane performance using ALD coated tubes is improved compare to an uncoated nanotube array. Further improvements in ALD or CVD reinforced nanotube arrays may increase the performance of nanotube membranes up to two orders of magnitude and reach the theoretical limit of channel density of $10^{12}$ tubes/cm$^2$ because it may eliminate or further reduce membrane blockage due to bent or 'pinched' tubes.

Examples of nanotube membranes may be found in, for example, U.S. patent application Ser. No. 13/654,057, filed Oct. 17, 2012, entitled "Preparation of aligned nanotube membranes for water gas separation applications." All aforementioned applications are hereby incorporated by reference in their entirety for any purpose.

Figure 2:
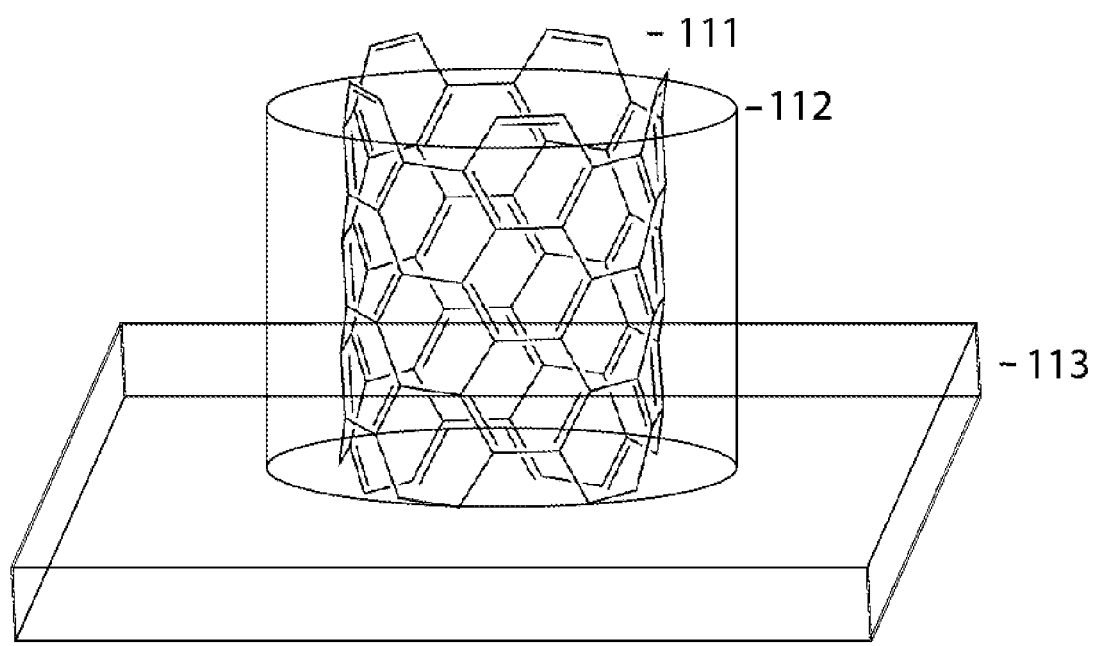
FIG. 2 is a schematic of a nanotube coated with an inorganic support layer and surrounded by polymer fill.

Example membranes described herein may include aligned carbon nanotubes coated with an inorganic support material and surrounded by polymer that fills gaps between the nanotubes. A block diagram of an example membrane 110 is illustrated in FIG. 1. Aligned carbon nanotubes 111 may be coated with an inorganic support material 112 and surrounded by polymer 113. A schematic of a terminus of a nanotube in an example membrane is illustrated in FIG. 2. Nanotube 111 may be coated with inorganic support material 112 and surrounded by polymer 113. Note that only the terminus of the nanotube is shown in FIG. 2. It is to be understood that the depicted nanotube would extend further into the polymer 113 which would be disposed between the nanotube 111 and other nanotubes in the aligned nanotube array. The aligned carbon nanotubes may be multi-walled carbon nanotubes, single-walled carbon nanotubes, or combinations thereof. The nanotubes may have diameters between 1-20 nm, although other diameters may be used in other examples. The inorganic support material is generally selected as a material that may be deposited to coat the carbon nanotubes and may provide some structural support to the carbon nanotubes. The inorganic support material may an inorganic oxide. Example inorganic support materials include, but are not limited to, alumina, titania, silica, hafnia, or combinations thereof, for example. The inorganic support material may be deposited by atomic layer deposition (ALD), chemical vapor deposition (CVD) or physical vapor deposition (PVD). The inorganic support material may coat the entire length of the nanotubes in some examples, or may coat portions of the length of the nanotubes in other examples. The inorganic support material may have an average thickness of 0.25-10 nm in some examples. The polymer may be implemented using epoxy, epoxy resin, polystyrene, aramid, polysulfone, or combinations thereof in some examples. The total membrane thickness may be 10-50 microns in some examples. The carbon nanotubes may extend along the entire thickness of the membrane. The membrane may or may not be mounted on a mesh or fabric for mechanical support. Other layers may be used in other examples.

Figure 3:
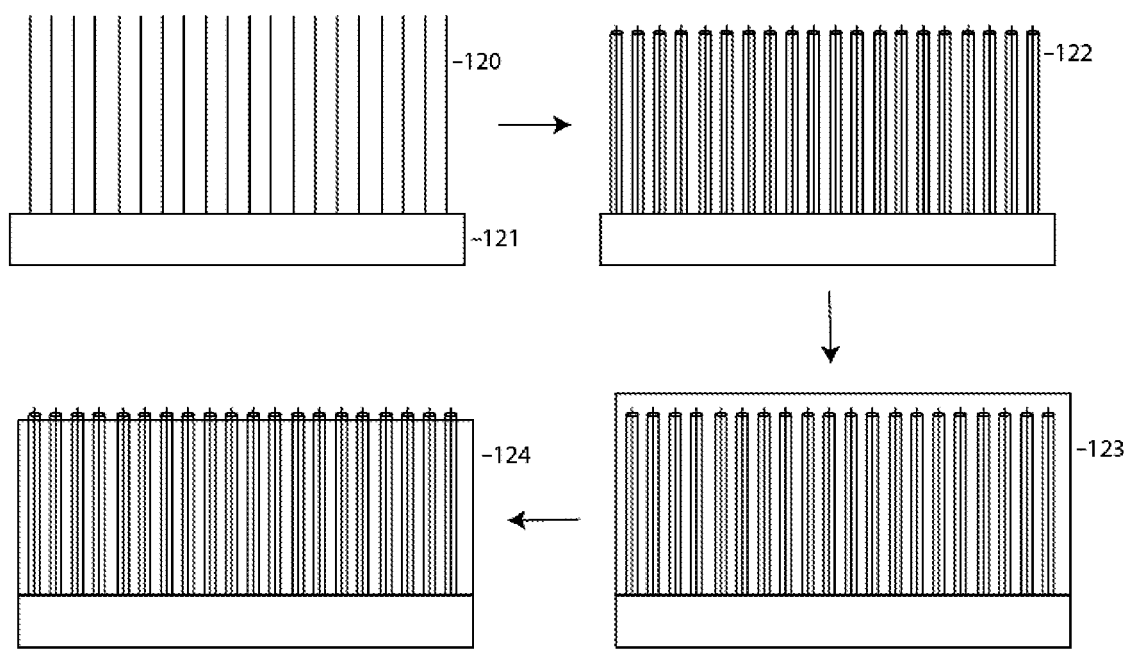
FIG. 3 is a schematic of an example method of fabrication of an aligned carbon nanotube membrane with an inorganic support layer and a polymer fill.
Figure 4:
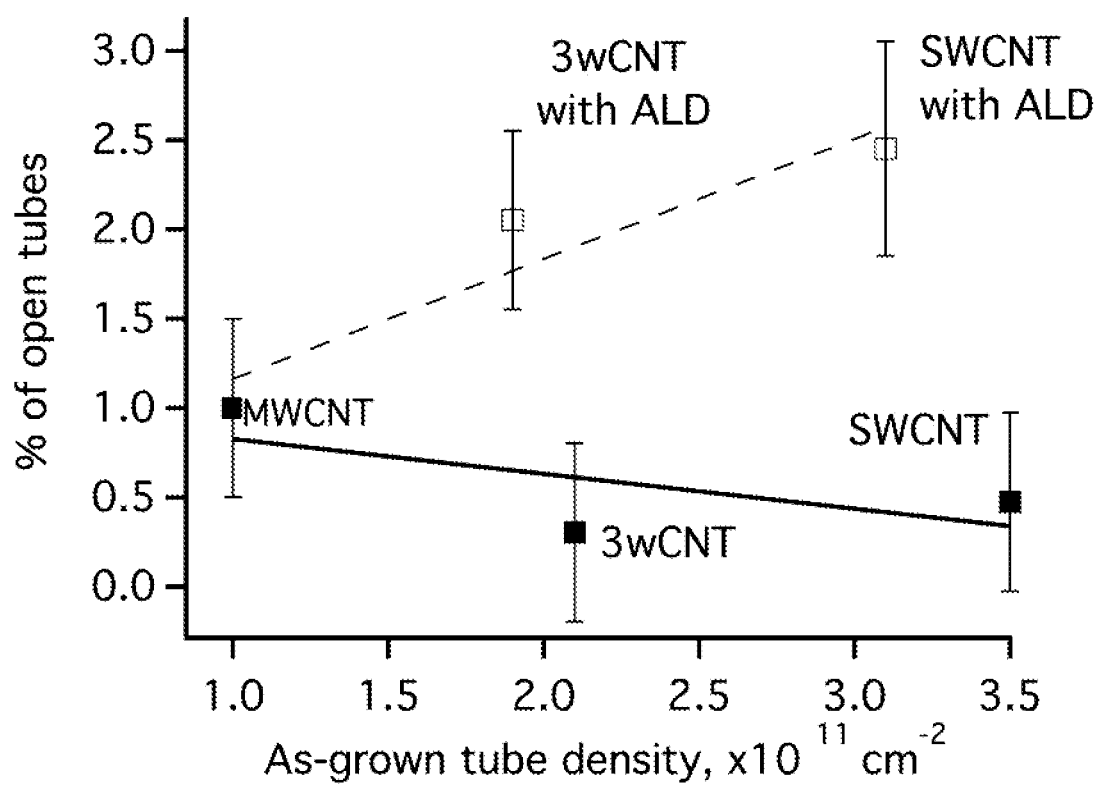
FIG. 4 is a plot of channel density from ion transport experiments vs as-grown nanotube density for various nanotubes.

A block diagram of an example method of fabrication is illustrated in FIG. 3. In one example, nanotube membrane 111 may be fabricated by growing an aligned array of carbon nanotubes 120 on silicon wafer 121. For example, the carbon nanotubes may be grown using 0.5 nm of Fe as a catalyst deposited over 30 nm of alumina on the silicon wafer 121. Other catalysts may be used in other examples. The catalyst may be deposited in a Semicore e-beam evaporator using very slow, 0.01-0.02 nm/s deposition rates. The catalyst may be annealed in Aixtron's BlackMagic™ cold wall CVD reactor using 700 seem H2 flow at 510° C. 10 mbar for 3 min followed by nanotube growth at 90 mbar synthesis pressure and growth temperatures of 700-725° C. using acetylene as a carbon source gas flowing at 5 seem. Other deposition and/or annealing techniques may be used in other examples. The nanotubes may be 30-45 microns tall and may have a diameter of 1.5- 3.5 nm with one to three tube walls in some examples. In some examples, the nanotubes may not be grown on the substrate, but may be provided as an aligned array through some other technique.

The nanotubes may be supported with an inorganic support material 122. In the example shown in FIG. 3, the inorganic support material 122 may be implemented using alumina, however, other inorganic materials may be used in other examples. The alumina support layer may be deposited using Oxford Instruments remote plasma ALD system. In some examples, a water with an aligned nanotube forest may be heated to 100° C. in vacuum and the alumina precursor (trimethylaluminum, TMA) may be added for 100 ms by bubbling nitrogen at 20 seem through the TMA solution. The TMA may remain at a chamber pressure of 15 mbar for 3-4 seconds to diffuse into the nanotube forest and to react with the carboxylic acid functional groups on the nanotube walls. Then the wafer may be purged and oxidized using remote oxygen plasma. Holding the TMA diffusion step for 1- 2 seconds may aid in infiltrating the nanotube array due to the high nanotube aspect ratio and the small average distance between individual nanotubes on order of 10 nm). The cycle may be repeated until the desired alumina film thickness is achieved (typically 150-200 cycles).

Accordingly, in examples described herein, inorganic support materials may be deposited onto carbon nanotubes within an aligned array of carbon nanotubes by performing atomic layer deposition. During atomic layer deposition, an inorganic support material precursor may be brought into contact with the aligned array of nanotubes under a pressure and flow rate sufficient to allow the precursor to diffuse into the aligned array of nanotubes and react with some or all of the nanotube walls. In this manner, the inorganic support material may be deposited onto some or all of the length of the nanotube walls. Other deposition techniques (e.g. CVD) may be used in other examples. In some examples, nanotubes may be coated with an inorganic support material prior to being formed into an aligned array (e.g. inorganic support material may be deposited on nanotubes which may not be in an aligned array and self-assembly or other techniques may be used to form an aligned array from nanotubes having a coating of inorganic support material).

Referring again to the example of FIG. 3, the nanotubes and alumina support may be infiltrated with polymer solution and then cured to form polymer 123. The polymer 123 may partially or fully cover the nanotubes and alumina support. In some examples the polymer solution may be an epoxy solution such as Bondit™ B45 or Epon 862. The epoxy solution may be prepared using standard recipes and then preheated to 80° C. to reduce the viscosity. After infiltrating for 20 minutes, excess epoxy solution may be removed by spinning 1 minute in a spin coater at 500 rpm. The epoxy may be cured at 80° C. overnight to form the polymer 123.

Accordingly, in examples described herein, polymer may be provided between the aligned nanotubes to form a membrane allowing transport through the nanotubes. In some examples, some transport may occur through the polymer. The polymer may be provided between the aligned nanotubes by infiltrating the aligned nanotubes with polymer solution and then curing the polymer solution. Infiltrating the aligned nanotubes with the polymer solution generally refers to providing polymer solution between the outside surfaces of the nanotubes in the aligned nanotube array. While in the example of FIG. 3 the polymer precursor is infiltrated around an existing aligned nanotube array, in some examples, nanotubes and/or nanotubes with inorganic support material may be provided in a polymer precursor solution, aligned through an alignment technique, and then the polymer solution cured to form the membrane.

Referring again to the example of FIG. 3, excess polymer 123 covering the nanotubes may be removed to expose the ends of the nanotubes to form an aligned nanotube polymer composite 124. The polymer may be removed (e.g. planarized) using mechanical and/or chemical-mechanical polishing techniques. For example, an Okamoto wafer grinding machine may be used to form a polished nanotube polymer surface. The wafer speed may be 100 rpm, the grinding disk speed may be 240-320 rpm, and the epoxy removal rate may be 10-30 µm/min. Diamond grinding disks with grid 320, 800 and 2000 may be sequentially used to achieve a final nanotube composite thickness of 10-25 µm. Triton X aqueous solution (0.1 mM) may be used as lubricant/cooling fluid during grinding. The quality of the polished surface may be inspected in optical and electron microscopes and measured using electrical conductivity: for a well-polished layer with exposed nanotube's resistance between wafer and top layer of polymer/nanotube composite may be 2-15 kOhm, while an underpolished water surface may be insulating. In some examples, polishing the nanotube composite may expose and may open the carbon nanotubes, which may improve transport through the composite in some examples.

Immersing the nanotube polymer composite 124 in a solution of 10% HF for typically 20 to 60 minutes may release the silicon wafer and nanotube membrane 110. The membrane may be washed in DI water for 5 to 10 minutes. Any catalyst residue transferred from the wafer may be removed by soaking the membrane overnight in 5% HCl solution.

Membranes described herein may be used as ultrafiltration membranes where defined pore size or high flux is advantageous (e.g. size separation) or for drug delivery. For example, the membrane may be used to separate a larger molecule of 2-20 nm (e.g. DNA, proteins, drugs, dietary supplement, or nanoparticles) from solution. The larger molecule would be rejected and the solvent or smaller molecules (e.g. unused reagents, salts, or contaminants) would pass through. Additionally, the membrane may be used to control the delivery of a drug (such as nicotine, insulin, or chemotherapy drugs) through electrophoretic transport. The drug would pass through the membrane with the drug flow rate or on/off ratio controlled by the applied bias.

What is claimed is:

1. A carbon nanotube membrane comprising:
   an aligned array of carbon nanotubes;
   an inorganic support material coating at least a portion of a length of the carbon nanotubes in the aligned array to form coated carbon nanotubes; and
   a polymer material disposed between the coated carbon nanotubes.

2. The carbon nanotube membrane of claim 1, wherein the inorganic support material comprises inorganic oxide.

3. The carbon nanotube membrane of claim 1, wherein the inorganic support material comprises alumina.

4. The carbon nanotube membrane of claim 1, wherein the polymer material comprises epoxy.

5. The carbon nanotube membrane of claim 1, wherein the polymer material is disposed in spaces between the inorganic support material coating at least a portion of a length of the coated carbon nanotubes.

6. The carbon nanotube membrane of claim 1, further comprising a mesh or fabric support supporting the polymer material.

7. The carbon nanotube membrane of claim 1, wherein the aligned array of carbon nanotubes, the inorganic support material, and the polymer form a carbon nanotube polymer composite having a surface, and wherein the surface is planarized.

8. The carbon nanotube membrane of claim 1, wherein the aligned array of carbon nanotubes have open ends at the surface.

9. The carbon nanotube membrane of claim 8, wherein the aligned array of carbon nanotubes extend through a thickness of the carbon nanotube polymer composite.

10. A method comprising:
    providing an aligned array of nanotubes;
    depositing an inorganic support material on at least some walls of the nanotubes in the aligned array;
    infiltrating a polymer precursor around the aligned array of nanotubes including the inorganic support material on at least some walls; and
    curing the polymer precursor to form a polymer nanotube composite.

11. The method of claim 10 wherein said providing an aligned array of nanotubes comprises growing the aligned array of nanotubes on a substrate.

12. The method of claim 10 wherein said depositing comprises using atomic layer deposition.

13. The method of claim 10 wherein said depositing comprises using chemical vapor deposition.

14. The method of claim 10, further comprising planarizing the polymer nanotube composite by mechanical polishing.

15. The method of claim 11 wherein the aligned array of nanotubes are provided on a substrate, the method further comprising releasing the polymer nanotube composite from the substrate.

16. The method of claim 10 wherein the inorganic support material comprises alumina, titania, silica, hafnia, or combinations thereof.

17. The method of claim 11 wherein the polymer precursor comprises an epoxy resin.

* * * * *